United States Patent [19]

Montesi et al.

[11] 4,271,538
[45] Jun. 9, 1981

[54] SAFETY SPECTACLES

[75] Inventors: Edward N. Montesi, Barrington; John H. King, Coventry, both of R.I.

[73] Assignee: Norton Company, Worcester, Mass.

[21] Appl. No.: 133,366

[22] Filed: Mar. 24, 1980

[51] Int. Cl.³ .............................................. A61F 9/02
[52] U.S. Cl. ........................................ 2/439; 2/447; 2/450
[58] Field of Search ............... 2/439, 431, 427, 448, 2/449, 451, 9, 444, 447, 450; 351/169, 44, 153; D2/234

[56] References Cited

U.S. PATENT DOCUMENTS

| D. 136,847 | 12/1943 | Cardona | D2/234 |
|---|---|---|---|
| D. 202,130 | 8/1965 | Mitchell | D57/1 |
| 1,225,548 | 5/1917 | Willson et al. | 2/449 |
| 2,274,791 | 3/1942 | Huggins | 2/444 |
| 2,296,634 | 9/1942 | Fink | 2/447 |
| 2,668,291 | 2/1954 | Schauweker | 2/450 |
| 3,156,756 | 10/1964 | Seaver | 2/450 X |
| 3,526,449 | 9/1970 | Bolle et al. | 351/44 X |
| 3,705,760 | 12/1972 | Langendorfer et al. | 2/427 X |
| 3,744,887 | 7/1973 | Dunbar | 351/153 |
| 4,062,629 | 12/1977 | Winthrop | 351/169 |

FOREIGN PATENT DOCUMENTS 753789   3/1967   Canada .................................... 2/449

*Primary Examiner*—Peter P. Nerbun
*Attorney, Agent, or Firm*—Walter Fred

[57] ABSTRACT

Safety spectacles (10) comprising a one piece flanged and curved front face piece (12) adapted to wrap around the forehead to the wearers temples. The face piece (12) is provided with a nose piece (14), a substantially distortion free spherical viewing and eye shield front wall portion (16) of varying thickness, an upper protective flange (18) and opposite side portions (20) with upper and lower flange portions (22) (24) including pivot pin receiving apertures therein pivotally hinged to temple bars (30). Each temple bar is provided with upper and lower pivot pins (32) projecting outwardly from upper and lower extensions of flanges (36) (38) extending inwardly from a relatively wide forward portion of the side wall (40) with or without vents or louvers (L). At least one pivot pin on each temple bar (3) and its receiving aperture each have an elongated or oblong shape with opposite rounded ends and tapered surface on one side thereof adapted to matingly engage and interlock with one another when the temple bar is pivoted to the wearing position.

15 Claims, 8 Drawing Figures

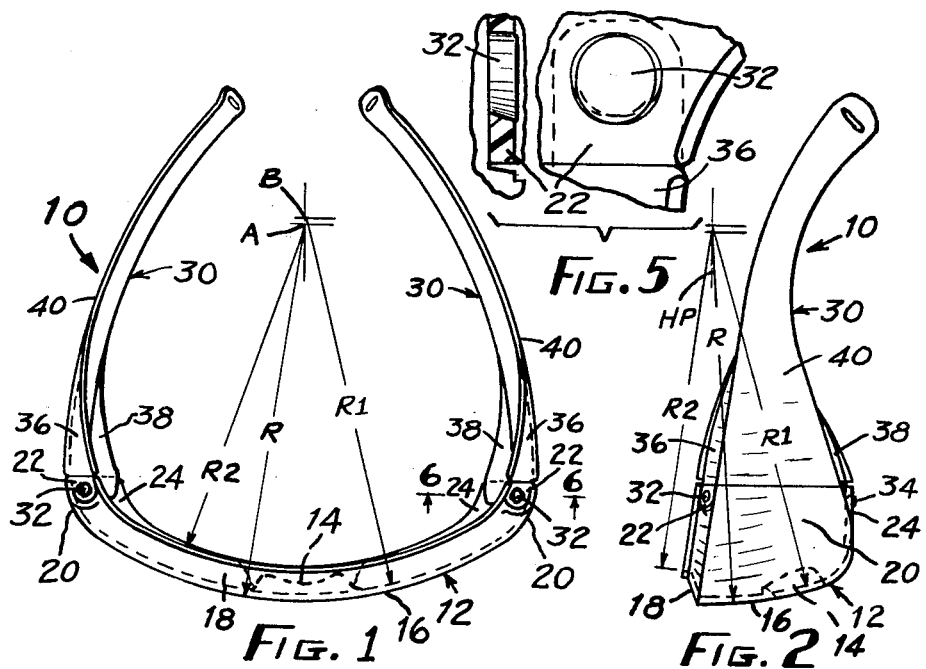
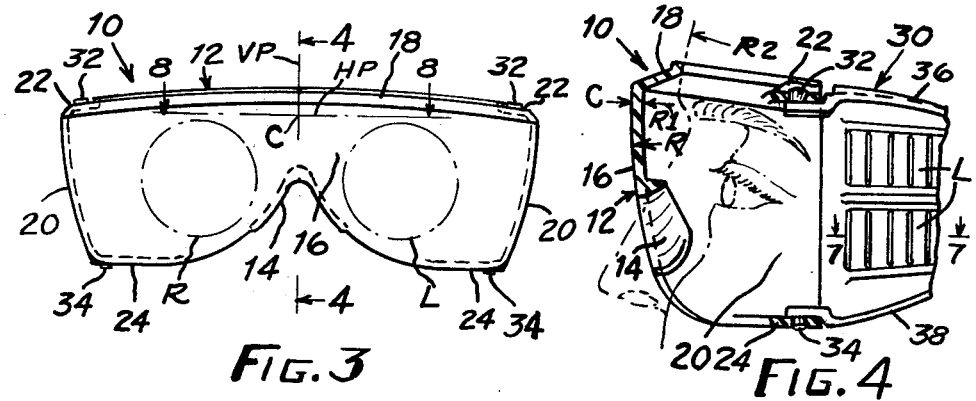
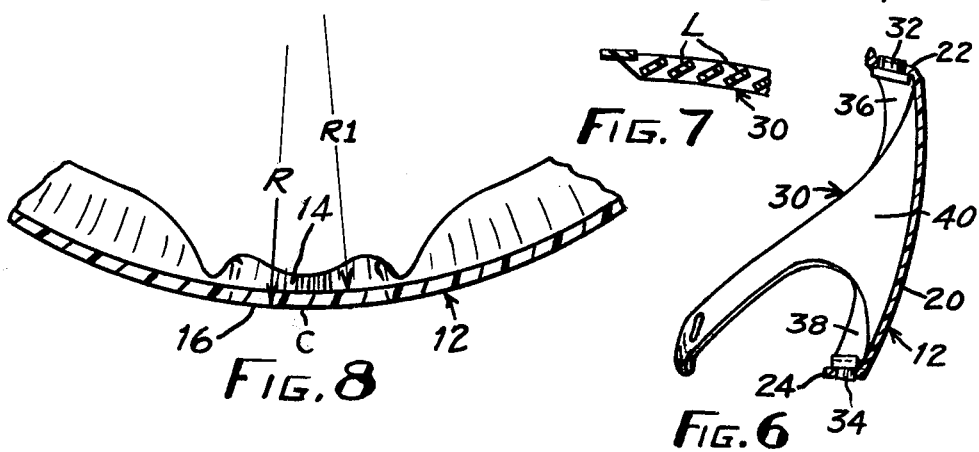

SAFETY SPECTACLES

TECHNICAL DISCLOSURE

The invention relates particularly to improved plano type industrial plastic safety spectacles or goggles having a one piece front face piece including a nose piece portion, a substantially distortion free transparent coated spherically curved viewing and eye shield portion and protective flange portion which wraps around the forehead to temple areas and pivotally hinged to one piece wide inwardly flanged temple bars including the hinge pivot pins whereby the wearers eyes, portions adjacent the eyes and the temples are enclosed and protected from injury.

BACKGROUND OF THE INVENTION

The prior art discloses a number of transparent plastic eye shields, sunglasses, goggles and spectacles with a one piece front hinged to narrow as well as wide flangeless temple bars and side guards or shield.

However, the primary purposes thereof is to protect the eyes from dust, wind, rain, sunlight and glare and in some cases are merely for ornamental or fashionable purposes. Hence, they do not provide adequate protection against the more dangerous industrial hazards and impact of flying objects or particles associated with construction or manufacturing processes and accidents.

Further, the prior art one piece front face piece members do not have a single spherically curved eye shield portion of high optical quality and hence has a tendency to distort the image viewed therethrough at various angles.

Although some front members have a flange which engages the forehead, the temple bars hinged thereto do not have curved protective flanges continuing around the temporal area from curved ends of the front member.

The plano spectacles of the invention are also provided with integrally molded plastic hinges. They differ from prior art hinges in that the temple bar pivot pins and the pivot pin receiving apertures on the front member or face piece have an elongated or oblong, interlocking and interfitting shape with outwardly extending mating tapered surfaces on one side thereof. Thus, they are interlocked and, a slight resistance to unintentional relative pivoted movement is provided to maintain them in the wearing position.

Further, the one-piece protective front of the applicants spectacles has a number of advantages with respect to both protection and optical characteristics.

Mechanically it offers the strength of tough polycarbonate optics and frame fronts since the two are combined. It eliminates the danger of lens displacement and provides excellent protection above and to the sides of the optical area.

Safety spectacles without side shields offer limited protection. Conventional side shields are awkward and restrict vision. The applicants spectacles offers a very wide visual field; the same continuous field as a 66 mm lens would offer—greater than any conventional safety spectacle and does this with no nasal interruption. The full field of view is a safety factor in itself.

Also, the one-piece front design offers visual advantages in acuity and comfort unlikely to be provided by a spectacle system consisting of a frame with two independent lenses. These advantages stem from the inherent control of the balance of optical effects between the two eyes. This is because with respect in small amounts of inherent power, prism, and astigmatic errors, the principal concern is imbalance between the eyes.

Power and astigmatic imbalance frustrate accommodation, lower acuity, and can cause space perception problems.

BRIEF SUMMARY OF THE INVENTION

Plano industrial type safety spectacles or goggles molded of tough transparent polycarbonate or fracture resistant plastic material comprises a single face piece or front protective member hinged to one piece pivotal resilient molded plastic temple bars. The front member comprises a nose piece portion, a single substantially distortion free transparent and coated high optical quality spherical viewing and eye shield portion of continuous varying thickness extending from a thick upper central point to areas and peripheral portions of lesser thickness engageable with facial portions adjacent the eyes, and temples. Also, integrally molded to the front member is an upper inclined protective shelf or flange portion that extends upwardly from the spherical eye shield portion and wraps around portions of the forehead and temple areas.

Each temple bar has a wide, curved forward side wall portion including upper and lower protective flanges, extending inwardly therefrom and rearwardly from an adjoining hinge pivot pin end portion and an end of a temple side portion of the front member to a rear side wall portion engageable with the head adjacent the ear. The temple bars have integrally molded elongated or oblong pivot pins insertable into and pivotable to interfering frictional engagement with internal surfaces of elongated or oblong pivot pin bearing apertures in opposing spaced flanges at opposite temple side portions of the front member.

Additionally, the elongated or oblong pivot pins and apertures have mating outwardly tapered surfaces on one side and when aligned into mating engagement tend to prevent relative vertical movement and separation thereof and unintentional relative pivotable movement.

BRIEF DESCRIPTION OF THE DRAWINGS

FIG. 1 is a plan view of the plano type safety spectacles of the invention;

FIG. 2 is a side view of the safety spectacles shown in FIG. 1 having plain non-perforated or louvered temple bars;

FIG. 3 is a front view of the safety spectacles shown in FIGS. 1 and 2;

FIG. 4 is a vertical cross sectional view taken along line 4—4 of FIG. 3 and through the center of the one-piece front member of the spectacles to show the spherical curvature and fit thereof relative to facial portions of a person depicted therein and an inside view of a portion of a right hand louvered temple bar hinged to the front member;

FIG. 5 is a combined partial plan and sectional view of a hinge portion showing the relative positions of the tapered elongated or oblong pivot pin and pivot pin bearing receiving aperture when the temple bars are pivoted to the open or wearing position;

FIG. 6 is a vertical cross sectional view of a hinge portion taken along line 6—6 of FIG. 1 showing upper and lower pivot pins, the side wall curvature and upper and lower curved protective flanges of a temple bar;

FIG. 7 is a partial horizontal cross sectional view through a louvered portion of a temple bar taken along line 7—7 of FIG. 4; and FIG. 8 is a partial horizontal cross sectional view through the spherical eye shield and viewing portion of the front member taken along line 8—8 of FIG. 3 and showing the spherical curvature of both the inner concave and outer convex surfaces and varying wall thickness thereof.

DETAILED DESCRIPTION OF THE INVENTION

Improved plano industrial type plastic safety spectacles or goggles 10 according to the invention are shown in FIGS. 1, 2 and 3. The safety spectacle or goggle 10 comprises a one piece molded plastic front member 12 including an inwardly extending notched or slotted nose piece portion 14, a transparent substantially distortion free spherical concave-convex viewing and eye shield or front wall portion 16, an upper inclined protective shelf or flange portion 18 and opposite flanged and curved right and left hand temple side or temple hinge portions 20.

The viewing and eye shield portion 16 has an outer spherical or convex surface with a single spherical radius of curvature R of about 5.033" (12.78 cm) from a point A of the intersection of a vertical plane VP passing through the center and a horizontal plane HP passing through the upper portion and central point slightly below and adjacent the junction with flange 18. An inner spherical concave surface of the spherical viewing and eye shield portion 16 has a slightly shorter single spherical radius of curvature R1 of about 5" (12.7 cm) from a point of intersection B of the vertical plane VP and the horizontal plane HP located about 0.057" (1.448 mm) rearwardly from point A. As a result the spaced spherical convex and concave surfaces extend outwardly from each side of the plane VP and downwardly from the horizontal plane HP and accordingly slightly varies the wall thickness of the viewing and eye shield portion 16.

As shown in FIGS. 3, 4 and 8 the wall thickness of the spherical viewing and eye shield portion 16 becomes thinner and varies continuously at a constant rate in all directions from its thickest point C of about 0.090 (2.286 mm) located adjacent the nose piece and upper flange at the junction of the vertical plane VP and horizontal plane HP.

Hence, all points of portion 16 including the center of each of the viewing areas or zones R and L therein, which are located the same radial distance from the thickest point C will be slightly thinner and of substantially the same thickness.

However, from an arcuate plane of fixed radius passing through the center of the viewing portions R and L, the wall gets thicker on the inner side of the arcuate plane toward the point C. Conversely, the wall on the outer opposite side of the arcuate plane leading away from point C becomes thinner.

In accordance with the laws of refraction of light rays through transparent materials and lenses with spherical convex and concave surfaces, the slightly varying wall thickness of the viewing areas R and L has the advantage of reducing distortion when viewing the object at various angles therethrough.

The continuous inclined shelf or flange portion 18 including an inner rim or rib is about 0.469" (1.18 cm) wide and has a concave surface with a radius of curvature R2 of about 4.564" (11.6 cm) from point A substantially parallel to radius R and outer convex surface.

Extending continuously from a point or line of tangency with the inclined shelf portion 18 and eye shield portion 16 are the opposite right and left hand temple hinge side portions 20 which wrap around to the temporal areas of the head. Each temple hinge portion 20 has opposed upper and lower curved hinge flange portions 22 and 24 with opposing aligned hinge pivot pin bearing apertures therein of which at least one or both have an eccentric, oblong or elongated circular form as shown in FIG. 5.

Additionally, each temple hinge portion 20 has an outwardly curved eye and temple protective side wall of substantially uniform thickness with a radius of curvature of about 1" (2.54 cm) to the outer convex surface extending between the upper and lower flanges and from the line or point of tangency with convex and concave surfaces of the front wall portion 16.

Each inwardly extending upper flange and rib on portion 20 is an extension of the upper flange and rib portion 18 and has an inner concave surface with a slightly greater radius of curvature than the outer convex surface of the side wall portion 20 taken from a different radial point. Hence, they are neither concentric or parallel to one another.

Extending inwardly from substantially the thinner lower side edge portions and inner concave surface of portion 16 and side portions 20 are the lower flanges 24 of substantially uniform thickness having an inner edge with a radius of curvature of about 1" (2.54 cm) taken from still another radial point.

The continuous inner concave edge or surface of the upper flange and rib 18 connecting the front portion 16, and temple hinge portions 20 is adapted to wrap around relatively close to the front and temple areas of the forehead above the eye.

Similarly, the continuous lower edges or surfaces connecting the lower thinner portions of front portion 16 and of the lower flanges 24 are adapted to come relatively close to front and side facial areas below and adjacent the eyes. Hence, the eyes and adjacent areas enclosed thereby are protected from possible injury.

Referring to FIGS. 1, 3, 4 and 6 the pivot axis of the aligned upper and lower oblong pivot pin bearing apertures in flanges 22 and 24 are inclined relative to the vertical plane VP whereby the lower pivot pins and apertures and flange 24 are situated closer to the plane VP. However, as seen from the side the pivot axis is substantially parallel to the vertical end surface of the portion 20 lying on a vertical plane extending perpendicular or normal to vertical plane VP.

As shown in FIGS. 4, 5 and 6 the oblong pivot pin aperture in the upper flange 22 is slightly larger than the pivot aperture in the lower flange 24. Also, the pivot apertures have internal bearing surface portions that are tapered or inclined on at least one or a rear side relative to the pivot axis.

Each elongated pivot aperture has a small entrance end that is longest or widest along a plane extending through the pivot axis situated at right angles to the vertical plane VP and parallel to the end surface of the portion 20 and is shortest or narrowest along the plane of the inclined pivot axis.

Pivotally hinged or attached to the right and left hand temple hinge side portions 20 are right and left hand temple bars or bows 30 preferably molded of a tough transparent polycarbonate or equivalent fracture resistant plastic material.

Each temple bar 30 is preferably a single or one piece unit comprising opposing upper and lower integral pivot pins 32 and 34 extending in opposite directions from forward hinge pivot pin portions or extensions of upper inclined and lower ribbed flange portions 36 and 38 extending inwardly from an outer curved side wall portion 40. However, the flanges 36 and 38 may be straight, inclined or curved to match the adjacent similarly straight, inclined or curved flanges 18, 22 or 24 of the face piece 12.

The side wall portion 40 has an outer convex surface and an inner concave surface and extends arcuately from a forward edge or end surface of a relatively wide forward end portion adapted to abut the end surface of portion 20 at the hinge joint to the rear end of a relatively narrower resilient rear end portion of the side wall portion 40 and temple bar 30.

As shown in FIG. 4 the wide forward side wall portion 40 of the temple bar 30 may be provided with air vents, holes, apertures or louvers L as shown in FIG. 7 or without them as shown in FIG. 2. However, louvers and narrow slots or passages therebetween situated at an angle to the side wall 40 are preferred for providing the greatest protection against the passage of and injury by particles directed toward the temple bars 30, and for circulating of air and escape of vapors which tend to fog up the viewing portions of the front member.

Referring to FIGS. 4, 5 and 6, at least one and preferably both pivot pins 32 and 34 of the temple bars 30 are also of tapered oblong shape, inserted into and retained in mating tapered oblong pivot apertures in the flange portions 22 and 24 of the front member 12. The lower pivot pins 34 and apertures have on one or rear side thereof mated tapered rear surface portions extending downwardly and diverging away from the pivot axis at an angle of about 15° and opposite surface portions parallel to the pivot axis.

Likewise, the upper pivot pins 32 and apertures which are of slightly greater size than the lower pin 34 and apertures have on one or rear side thereof mated tapered rear surface portions extending upwardly and diverging away from the pivot axis at an angle of about 15° and opposite surface portions parallel to the pivot axis.

The pivot axis is also inwardly inclined at an angle of about 8.5° relative to the vertical plane VP from the upper outer pivot pin 32 to the lower inner pivot pin 34.

As seen in FIG. 5 each oblong pivot pin has an inner cylindrical small end of a diameter substantially equal to the narrower and minimum width of the small end of the oblong pivot pin aperture. From the small end the pivot pin tapers on one side to a larger elongated or oblong end of a length substantially equal to the greater or maximum width of the large end of the tapered pivot pin aperture and no greater than elongated length of the smaller or entrance end of the oblong aperture through which the large oblong end of the pivot pin must pass. Hence, the temple bars 30 are attached to the front member 10 by positioning the temple bars 30 in the folded position at right angles to the wearing position shown whereupon the elongated pivot pins are aligned with the elongated pivot pin apertures. Then the resilient flange portions and the pivot pins projecting therefrom are forced or compressed toward each other, inserted between the upper and lower flanges of the hinge portion 30, aligned with and released into the apertures.

Pivoting of the temple bars 30 outwardly from the folded position aligns the mating tapered surface portions of the pivot pins and apertures which tend to maintain them in the wearing position.

As seen in FIGS. 1, 2 and 6 the temple bars 30 are curved inwardly toward each other and the vertical plane VP and also downwardly inclined and curved from the horizontal plane HP. When the spectacles or goggles 10 are applied to the head the resilient rear side wall portions of the temple bars resiliently or yieldingly engage and frictionally grip against side portions of the head adjacent the ears.

Preferably, the rear ends of the temple bars may be slotted as shown and if desired or necessary connected by adjustable elastic or resilient means such as a band or cord (not shown).

The elastic means would engage the back of the head, tension and maintain the spectacles or goggles and protective flanges thereof wrapped around and against the forehead and temple areas of the head.

Additionally, the spreading apart of the temple bars 30 causes them to be forced into and resiliently maintained in abutting engagement with the end stop surfaces of the hinge portion 20 and thereby eliminate any space or opening at the hinge joint therebetween.

The abutting relationship at the hinge joint also maintains the inner curved edges or surfaces of the upper and lower protective flange portions 36 and 38 in alignment with the curvature of the inner edges or surfaces of the upper and lower protective flange portions of the hinge portions 20.

Thus, the high optical quality spectacles or goggles 10 of the invention with the closely fitting upper inclined and lower protective flanges on both the one piece front member 12 and temple bars 30 and the closely fitting nose piece and lower edge portion of the front member 12 tend to wrap around, enclose and provide very little, if any, space through which injurous particles can pass. Also, the outer convex like curvature of the tough molded plastic wall portions of the front member 12 and temple bars 30 and the inclined protective flange portions provide greater strength and resistance to impact and the tendency to deflect particles and objects therefrom.

Although, tough transparent polycarbonate is the preferred molded plastic material, the spectacle front member and temple bars may be injection molded of the same or different suitable impact or fracture resistant plastic material selected from a group consisting of polycarbonate methyl methacrylate, cellulose propionate, cellulose acetate and cellulose butyrate.

Further, the front member 12 may be molded of either clear or color tinted transparent plastic material and the temple bars of either clear, color tinted, opaque or translucent plastic material. Also, the transparent plastic front members 12 and, clear temple bars may be tinted with color to reduce glare and/or coated with a transparent clear layer of abrasion resistant material suitable to reduce scratching thereof and scattering of light rays therefrom.

Preferably, the entire outer spherical convex surface of the front viewing and eye shield wall portion 16 and convex surfaces of the temple hinge portion are uniformly coated with a very thin layer of a clear transparent abrasion resistant material about 3 to 5 microns thick. The thin coating is applied in the well known conventional manner and has the known effect of reducing scratching and scattering of light rays and thereby allowing more light to pass therethrough.

The coating may be any suitable material such as disclosed in U.S. Pat. Nos. 3,986,997; 4,027,073; 3,451,838; 3,868,434 and 3,862,261 and preferably an abrasion resistant composition A.R.C., commercially available from Dow Corning Corp., Midland, Mich.

Further, the refractive power of each of the viewing zones R and L is preferably within ±1/32 (0.031) diopters and the maximum astigmatism in any median thereof is preferably less than and not greater than 1/16 (0.0625) diopters.

The resultant of the vertical and horizontal prismatic imbalances are also preferably not greater than ¼ (0.250) diopters.

As measured in accordance with Federal Test Standard 406, Method 3022, haze in at least the viewing portions R and L is preferably less but not greater than 6% or put another way, the viewing portions are from 96% to 100% of being absolute clear and free of haze.

Definition of the viewing zones R and L when checked with a telescope placed at the prescribed distances on the axis of viewing zone R and L and focussing on a National Bureau of Standards special publication #374 High Contrast Test Chart Pattern #20 is preferably clearly resolved in both orientations.

However, the following TABLE I shows the preferred "as worn" specification or tolerances for the single transparent spectacle front wall of the invention molded of polycarbonate and based on 1. a refractive index of 1.586
2. an outer spherical radius R of 5.033" (12.78 cm)
3. an inner spherical radius R1 of 5" (12.7 cm)
4. a continuously varying lens thickness of 0.090" (2.286 mm) maximum thickness
5. a pantoscopic angle of 8°
6. a target distance of 420" (10.668 m)
7. an interpupillary distance of 2.68" (68 mm) between eyes

TABLE I

| Power | ±0.03 | diopters |
| --- | --- | --- |
| Astigmatism | 0.06 | diopters (max) |

TABLE I-continued

| Power imbalance | 0.09 | diopters |
| --- | --- | --- |
| Astigmatism imbalance | 0.06 | diopters |
| Vertical prism imbalance | .125 | prism diopters |
| Horizontal negative (−) Base in prism imbalance | 0.25 | prism diopters (max) |
| Horizontal positive (+) Base out prism imbalance | 0.25 | prism diopters (max) |

The following Table II discloses data comparing the optical "as worn" tolerances of the safety spectacles of the invention with those of a number of known standards specifications. ("as worn" expressed or inferred from single lens specs.)

TABLE I

| Specification Power (Diopters) Prism (Prism (Diopters) | Power | Power Imbal. | Astig. | Astig. Imbal. | Vert. Prism Imbal. | Horiz. Prism Imbal. |
| --- | --- | --- | --- | --- | --- | --- |
| Safety Spectacles of the Invention | ±0.03 | 0.09 | 0.06 | 0.06 | 0.125 | 0.25 In(−) 0.25 Out(+) |
| ANSI Z87.1-1979 Assume Thickness of 3.4 mm, 8.0° Face Form Frame | ±0.06 | 0.12 | 0.06 | 0.12 | 0.125 | 0.125 In 0.52 Out In |
| ANSI Z80.1-1979 (Ophthalmic) | ±0.13 | 0.26 | 0.13 | 0.26 | 0.33 | 0.67 Out |
| ANSI Z80.3-1977 (Sun Glasses) | +0.12 to −0.25 | 0.18 | 0.18 | 0.18 | 95% less than 0.5 | 95% In Less than 0.5 Out |
| ISO TC94/SC6 Standard For Eye Protectors | Grade 1 ±0.06 Grade 2 ±0.12 | 0.12 0.25 | 0.06 0.12 | 0.12 0.25 | 0.25 | 0.25 In 1.00 Out |
| Mounted Lenses and Shields | Grade 3 ±0.12 to −0.25 | 0.25 | 0.25 | 0.25 (Axes Parallel) | | |

The data shows the spectacles of the invention to be a substantial improvement over and to exceed the other standards and specifications.

Further, it has been calculated and shown that the theoretical horizontal prism imbalance which can be expected from the transparent front wall portion 16 of zero (0) refractive power which becomes continuously thinner outwardly from its point of maximum wall thickness of 0.090" (2.286 mm) does not exceed 0.073 diopters at an eye sweep angle of 20° or less.

Under the same circumstances a similar transparent front wall portion with a constant wall thickness of 0.090" (2.286 mm) can be calculated and shown to have a greater horizontal prism imbalance that is never less than 0.430 diopters as well as a negative (−) refractive power of 0.053 diopters even when looking straight through the lens on the 0° axis.

As many possible embodiments and modifications of the invention are possible. It is to be understood that the embodiment described hereinabove and shown in the drawing is not to be interpreted in a limiting sense but includes all modifications and requirements thereof falling within the scope of the appended claims.

We claim:
1. Safety spectacles comprising:
    a single face piece including a continuous wall with an outer convex surface extending between opposite ends thereof molded of relatively tough fracture resistant plastic material adapted to protect a wearers eyes, extend in front of, around and beyond the eyes to opposite side temples of the wearer and inwardly toward facial portions adjacent the eyes and having
  a transparent front wall portion including
    right and left viewing zones, and a wall thickness that varies continuously in all directions across the viewing zones from a point situated in a plane between the viewing zones,
  a nose piece portion including a notch between the right and left viewing zones, opposite temple side portions each having
    a sidewall portion with an outer convex surface extending from the front wall portion to an opposite end of the face piece and a lower flange portion extending inwardly from the side wall to an inner surface thereof,
  a continuous upper flange portion extending inwardly from the front and opposite temple side wall portions to an inner surface thereof and adapted to wrap around the wearers forehead to the temples,
  temple bars pivotally hinged to the opposite temple side portions and each having
    a forward sidewall portion including an outer convex surface extending from a forward edge thereof adapted to abut an opposite end surface of the face piece to a rear side wall portion adapted for engaging a side portion of the wearers head adjacent an ear and
    upper and lower flange portions extending inwardly from the forward sidewall portion of the temple bar to an inner surface thereof whereby the upper and lower flanges and the forward side wall portion including the outer convex surface of the temple bars constitute extensions of the upper and lower flanges and the side wall portion including the convex surface of the opposite temple side portions of the face piece.

2. Safety spectacles according to claim 1 wherein the transparent front wall portion further comprises:
  a smooth outer convex surface with a single spherical radius of curvature.

3. Safety spectacles according to claim 2 wherein the transparent wall portion further comprises:
  a smooth inner concave surface with a single spherical radius of curvature.

4. Safety spectacles according to claim 3 wherein the transparent wall portion has
  a predetermined wall thickness that varies continuously from its thickest point situated adjacent the nose piece and the upper flange.

5. Safety spectacles according to claim 1 wherein each of the opposite temple side portions further comprises:
  an upper pivot pin receiving aperture in the upper flange and a lower pivot pin receiving aperture in the lower flange.

6. Safety spectacles according to claim 5 wherein each of the temple bars further comprises:
  an upper pivot pin extending from a forward hinge portion of the upper flange and into the upper pivot pin receiving aperture and
  a lower pivot pin extending from a forward hinge portion of the lower flange and into the lower pivot pin receiving aperture.

7. Safety spectacles according to claim 6 wherein at least one of the pivot pins on each temple bar and at least one of the pivot pin receiving apertures on each temple side portion have
  an oblong shape including opposite rounded end portions and
  a tapered surface.

8. Safety spectacles according to claim 7 wherein the tapered surface on at least one of the pivot pins and on at least one of the pivot pin receiving apertures are mating tapered surface portions thereof situated on one side of a plane passing through a pivot axis of the pivot pins and pivot pin apertures.

9. Safety spectacles according to claim 8 wherein the oblong shape pivot pin receiving aperture further comprises:
  an outer large oblong end of predetermined maximum length and of shorter maximum width at an outer surface of the flange,
  an opposite inner small oblong end at an opposite inner surface of the flange of substantially the predetermined maximum length but of less maximum width than the shorter maximum width of the outer large oblong end and
  a tapered surface extending lengthwise along one side of and between the opposite rounded ends of the apertures and which tapers outwardly from the inner smaller oblong end to the outer large oblong end of the pivot pin receiving aperture.

10. Safety spectacles according to claim 9 wherein the oblong shape pivot pin further comprises:
  a large outer oblong end having a maximum length that is no greater than the maximum length of but greater than the maximum width of the inner small oblong end of the pivot pin receiving aperture and
  a small end adjoining the forward hinge portions of the flange having
    a maximum dimension, no greater than the maximum width of the inner small oblong end of the pivot pin receiving aperture and a tapered surface extending around one of the rounded end portions of the oblong shape pivot pin and tapering outwardly from the inner small end to the outer large oblong end of the pivot pin and adapted for mating engagement with the tapered surface of the pivot pin receiving aperture when the temple bar is pivoted to the wearing position whereby the outer larger oblong end of the pivot pin may be passed through the inner small oblong end of the pivot pin receiving aperture when the maximum lengths thereof are aligned with one another and the temple bar pivoted to a non viewing position.

11. Safety spectacles according to claim 10 wherein the transparent front wall portion further comprises:
  a smooth outer convex surface with a single spherical radius of curvature.

12. Safety spectacles according to claim 11 wherein the transparent front wall portion further comprises:
  a smooth inner concave surface with a single spherical radius of curvature.

13. Safety spectacles according to claim 12 wherein the transparent wall portion has
  a predetermined wall thickness that varies continuously from its thickest point situated adjacent the nose piece and the upper flange.

14. Safety spectacles according to claim 10 wherein temple bar further comprises:
  at least one vent passage.

15. Safety spectacles according to claim 14 wherein the temple bar further comprises:
  an inclined louver adjacent each vent passage.

* * * * *